United States Patent
Clerc

[19]

[11] Patent Number: 6,133,046
[45] Date of Patent: Oct. 17, 2000

[54] MICROSYSTEMS FOR BIOLOGICAL ANALYSES, THEIR USE FOR DETECTING ANALYTES, AND METHOD FOR PRODUCING THEM

[75] Inventor: Jean-Frederic Clerc, Le Fontanil, France

[73] Assignee: Commissariat a l'Energie Atomique, Paris, France

[21] Appl. No.: 09/331,578

[22] PCT Filed: Dec. 29, 1997

[86] PCT No.: PCT/FR97/02439

§ 371 Date: Jun. 30, 1999

§ 102(e) Date: Jun. 30, 1999

[87] PCT Pub. No.: WO98/29739

PCT Pub. Date: Jul. 9, 1998

[30] Foreign Application Priority Data

Dec. 30, 1996 [FR] France .................................. 96 16200

[51] Int. Cl.[7] ............................ G01N 33/566; C12M 1/34
[52] U.S. Cl. ..................... 436/501; 422/68.1; 422/82.01;
435/4; 435/6; 435/7.1; 435/7.92; 435/287.1;
435/817; 436/518; 436/524; 436/527; 436/526;
436/525; 204/400; 204/403; 204/206
[58] Field of Search ............................ 435/287.1, 4, 817,
435/6, 5, 7.1, 7.92, 7.93; 436/501, 536,
518, 524, 527, 532, 526, 525; 422/68.1,
90, 69, 83, 98, 676, 82.01; 204/400, 403,
198, 206, 225, 668

[56] References Cited

U.S. PATENT DOCUMENTS

| | | |
|---|---|---|
| 4,054,646 | 10/1977 | Giaever . |
| 4,822,566 | 4/1989 | Newman . |
| 5,492,020 | 2/1996 | Okada . |
| 5,567,301 | 10/1996 | Stetter et al. . |
| 5,744,719 | 4/1998 | Werner . |
| 5,846,744 | 12/1998 | Athey et al. . |
| 5,922,537 | 7/1999 | Ewart et al. . |

FOREIGN PATENT DOCUMENTS

| | | |
|---|---|---|
| 0 244 326 | 11/1987 | European Pat. Off. . |
| 0 605 300 | 8/1994 | European Pat. Off. . |
| 2 598 227 | 11/1987 | France . |
| WO 09/22889 | 10/1994 | WIPO . |

OTHER PUBLICATIONS

Baitaillard et al. (1988). Direct detection of immunospecies by capacitance. Anal. Chem. 60:2374–2379.

Database WPI, Derwent Publications, AN 96–396800, JP 8–128977, May 21, 1996.

C. Schyberg, et al., Sensors and Actuators B, vol. 26–27, pp. 457–460, "Impedance Analysis of Si/SiO2 Structures Grafted with Biomolecules for the Elaboration of an Immunosensor", 1995.

P. Bataillard, et al., Analytical Chemistry, vol. 60, pp. 2374–2379, "Direct Detection of Immunospecies By Capacitance Measurements", 1988.

*Primary Examiner*—Christopher L. Chin
*Assistant Examiner*—Minh-Quan K. Pham
*Attorney, Agent, or Firm*—Oblon, Spivak, McClelland, Maier & Neustadt, P.C.

[57] ABSTRACT

An apparatus for detecting an analyte in a sample, including a cell with at least one fixed electrode, at least one mobile electrode opposite the fixed electrode, the mobile electrode being configured to move with respect to the fixed electrode, and a sample receiving cavity defined by a space between the fixed electrode and the mobile electrode, wherein a surface of at least one of the fixed electrode and mobile electrode facing the sample receiving cavity is configured to bound a ligand of the analyte to be detected. The apparatus also includes a displacement mechanism configured to move the mobile electrode; and an external circuit connected to the fixed electrode and to the mobile electrode, and configured to measure a parameter having a value depending on the presence between the fixed electrode and the mobile electrode of the analyte to be detected.

19 Claims, 4 Drawing Sheets

MICROSYSTEMS FOR BIOLOGICAL ANALYSES, THEIR USE FOR DETECTING ANALYTES, AND METHOD FOR PRODUCING THEM

BACKGROUND OF THE INVENTION

1. Field of the Invention

The present invention relates to microsystems for biological analyses for use in the health sector, the food processing industry and the environmental sector.

It is particularly used to produce biological analyses microsystems intended for in vitro diagnostics in analyses of infectious illnesses such as detecting the HIV virus, mycobacteria etc.

In these fields, where it is important to cut costs in the health system, analysis microsystems are currently needed that have a single usage, that are easy to operate, that use only very small amounts of samples and that are based on principles of direct detection that require neither a detection reagent (marker or other means) nor amplification of a detection signal.

2. Discussion of the Background

Approximately four years ago new types of tests appeared such as multi-affinity tests, tests integrating functions such as gene amplification and separation using electrophoresis. The industrial applications of these new types of tests seem to be widespread even though at present they are mainly used in human genome sequencing.

The success of these new tests is mainly due to the micro-technologies that have been introduced into the biological field. Through being integrated and combined, the micro-technologies have enabled high performance levels to be reached and speeds and sensitivity levels to be increased. Furthermore, micro-technologies have led to new technical solutions such as miniaturization and integration and new economic solutions such as mass production, thus giving the development of biosensors new impetus.

For example, systems capable of directly performing immunochemical tests have recently been launched. These test systems consist of thin layers of a semiconductor material and silica with antibodies covalently bonded to these layers, said antibodies enabling the presence of an antigen to be detected that is capable of reacting with the antibodies by measuring the capacitance of the assembly (see reference 1: Battaillard et al., in "Analytical Chemistry", 60, 1988, pages 2,374 to 2,379). Another microsystem of the same type is described by Schyberg et al. in reference 2: "Sensors and Actuators", B26–27, 1995, pages 457 to 460.

The documents of reference 3: FR-A-598 227 and 4: EP-A-244 326 also describe a method for detecting and/or identifying a biological substance in a liquid sample by means of electrical measurements. According to this method, the sample is brought into contact with a reagent support plate that comprises a specific ligand of the biological substance to be detected. Said plate can be made of a semiconductor material such as silicon and can be coated with an insulating layer of silica. The constituents C and/or R are then measured for the electrical impedance of the system in order to detect whether the biological substance is present in the sample.

All these systems use the recognition reaction between the biological substance to be detected and a specific ligand of the substance to be able to detect said biological substance directly without other reagents or means of detection such as markers, signal amplification reactions, etc. having to be used. This recognition reaction causes an active layer to form that has electrical characteristics, for example a capacitance and an impedance that are different from those in the system without the said layer.

However, the systems that exist at present do not allow for any other measurement other than electrical impedance to be used and they are not suitable for measuring near to or within the active layer.

SUMMARY OF THE INVENTION

The present invention therefore relates to a microsystem for biological analyses that is based on the same principle, i.e. on the recognition reaction between the biological substance or analyte to be detected and a specific ligand that is capable of detecting this recognition reaction with several combined types of measurements. Said measurements consist in measuring impedance and rheological viscosity as well as surface forces. The microsystem is also capable of measuring near to or within the active analyte—ligand layer.

According to the invention the analyte detection or dosage apparatus comprises:

a cell comprising at least one fixed electrode and at least one mobile electrode opposite the fixed electrode, the mobile electrode being capable of displacement such that it can be brought close to and/or move away from the fixed electrode, the space between the electrodes constituting a receiving cavity for the sample and the surface of at least one of the electrodes opposite the receiving cavity being capable of bonding a specific ligand of the analyte to be detected, means for displacing the mobile electrode, means for connecting the electrodes separately to an external electric circuit, and means for measuring the impedance or the electrical capacitance between the electrodes.

Preferably, according to the invention, the mobile electrode and the fixed electrode are both capable of bonding a specific ligand of the analyte to be detected, the ligands of the two electrodes being identical or different.

Generally, at least one and preferably both of the electrodes are coated with a ligand.

In the apparatus of the invention, the means for displacing the mobile electrode can be constituted by means of polarization of the fixed electrode and the mobile electrode.

By applying a suitable voltage to said electrodes, a capacitance Fc can be created perpendicular to the surface of the electrodes. This capacitance can be expressed by the following equation:

$$Fc = \tfrac{1}{2} \epsilon S V^2 / e^2,$$

where $\epsilon$ is the dielectric constant of the medium between the electrodes, V is the voltage applied, e is the mean distance between the electrodes and S is the surface area of the electrodes.

This capacitance thus enables the mobile electrode to be displaced, providing that said mobile electrode is free to move within the apparatus.

According to one alternative of the invention the displacement means of the electrode are magnetic means.

According to the invention the displacement means of the mobile electrode can also consist of excitation means using an inductive effect. If excitation means are to be used, the mobile electrode can be connected to coils through which an electrical current passes and said coils subjected to a magnetic field such that a force is created that displaces the mobile electrode in the preferred direction.

In one embodiment of the invention the cell comprises a container on a surface onto which the fixed electrode is fastened. The mobile electrode is positioned opposite the fixed electrode on a movable part mounted on the surface(s) of the container using at least one flexible beam, such that the mobile electrode can be brought close to or move away from the fixed electrode by the beam becoming distorted. The electrical contacts are provided on the surface(s) of the container, on said flexible beam and on the movable part connecting the fixed electrode and the mobile electrode separately to the external electrical circuit. Said electrical circuit enables the electrodes to be polarized and the capacitance between the fixed electrode and the mobile electrode to be measured.

In this event the displacement means of the mobile electrode can be constituted by the polarization means of the fixed electrode and of the mobile electrode. However, it can be advantageous to use a second pair of electrodes as displacement means of the mobile electrode. Said second pair of electrodes are positioned respectively on the surface of the container and on the movable part such that they lie opposite one another and the polarization means of the pair of electrodes are such that they cause the movable part that supports the mobile electrode to move.

In this particular embodiment of the invention magnetic displacement means can also be used to displace the mobile electrode. In this event, said magnetic means can comprise a permanent magnet positioned on the movable part and means for applying a magnetic field to said magnet.

According to this particular embodiment of the invention, the apparatus is advantageously constructed using a silicon substrate that includes an embedded silica layer. In this event, the bottom and the surface(s) of the container are made of silicon, the surface(s) are separated from the bottom by a layer of insulating silica, the movable part and the flexible beams are also made of silicon and the electrodes are made of silicon that acts as a conductor due to the implantation of ions.

The apparatus of the invention is used to detect or to dose different kinds of analytes. As an example of the kinds of said analytes, particularly those found in the field of medicine, the invention can apply to antigens, haptens, antibodies, peptides, fragments of nucleic acid (DNA or RNA), enzymes and enzyme substrates.

According to the invention, in order to detect these analytes at least one of the electrodes is coated with a specific ligand of the analyte to be detected, for example using direct or indirect grafting of said ligand onto the electrode(s). When the electrode(s) thus coated comes into contact with a sample containing the appropriate analyte, an analyte—ligand complex or active layer is created on the electrode(s) and the presence of this complex is detected using various measurements, for example electrical impedance measurements or viscosity measurements or measurements of the contact force in relation to the sensitive layer.

The specific ligands that coat the electrode(s) are those that have at least one recognition site of the analyte and are capable of connecting to said analyte. The ligand-analyte pair can therefore belong to the following pairs: antigen-antibody, hapten-antibody, hormone-receptor, DNA-$DNA_c$, RNA-$RNA_c$, enzyme-substrate or any other combination of molecules, whether biological or not, that are capable of creating complexes between themselves.

According to the invention, the use of a detection apparatus comprising a mobile electrode offers a number of advantages.

The apparatus of the invention enables measurements to be made near to or within the active layer in a position close to the electrodes. This results in heightened sensitivity, enabling the distance between the electrodes to be small, for example from 0.1 to 0.5 $\mu$m.

Under these conditions, signal loss due to the presence of a larger quantity of liquid between the electrodes can be avoided. Accuracy is therefore improved.

On the other hand, when the electrodes are further away from each other, for example at a distance between 1 and 10 $\mu$m, the grafting operation of the ligand onto the electrode(s) can be made while avoiding the formation of clusters, thus enabling a uniform layer of ligands to be obtained that is as dense as possible.

Similarly, if the sample is brought into contact when the electrodes are in the remote position, the fluidics are simplified by allowing agitation of the fluid on the electrodes, resulting in increased probability of recognition between the analyte and the bonded ligand. The formation of clusters is also avoided and a dense, uniform active layer is obtained on the electrode(s).

Finally, the fact of having a mobile electrode also enables the presence of an analyte to be detected using other measurements, for example a measurement of the viscosity of the sensitive layer by studying the damping of movement of the mobile electrode in said layer after a series of alternate movements made by the electrode.

The presence of analyte can also be detected by measuring the mechanical force on the surface near the sensitive layer, as will be seen below.

The invention also relates to a method for detecting or dosing an analyte in a liquid sample that comprises the following stages:

a) introducing said sample in a cell that comprises at least one fixed electrode and at least one mobile electrode positioned opposite the fixed electrode, said mobile electrode being capable of displacement such that it is able to be brought close to or move away from the fixed electrode. At least one of the said electrodes is coated with a specific ligand of the analyte to be detected and the sample is positioned between the electrodes with the mobile electrode being in a position remote from the fixed electrode;

b) displacing the mobile electrode at least once in order for it to be brought close to the fixed electrode or for it to oscillate between a position close to and a position remote from the fixed electrode; and c) during said displacement or after said displacement(s), measuring a representative parameter of the formation, or absence of a formation, of a sensitive layer obtained from reaction of the ligand with the analyte to be detected, said formation being between the electrodes.

In a first embodiment of this method the mobile electrode is displaced once only or several times in stage b) in order for it to be brought close to the fixed electrode. In stage c), the electrical impedance between the electrodes is then measured after each displacement, the impedance measured being compared to a reference value that is set when the analyte is not present.

In this first embodiment of the method of the invention, several impedance measurements can also be made using different distances between the electrodes in order to obtain a reading of the phenomena of impedance variation due to the presence of the active layer formed by the ligand-analyte complex. The impedance of the intermediary layer and the impedance of the active layer can also be obtained separately.

In a second embodiment of the method of the invention that is specially adapted to measuring the viscosity of the sensitive layer in stage b), the mobile electrode is displaced several times in order for it to oscillate between a close position and a remote position then, after said displacements, the capacitance between the electrodes is measured over time in stage c).

This enables the damping of the movement of the mobile electrode to be measured as well as the difference of amplitude due to the friction created between the mobile electrode and the active layer that is dependent on the viscosity and thickness of said layer. The quality coefficient Q, that is directly linked to the loss of energy due to the friction and therefore to the viscosity, can therefore be calculated.

In a third embodiment of the invention that is particularly suitable for measuring the surface mechanical force in stage b), the mobile electrode is displaced once only in order for it to be brought close to the fixed electrode. In stage c) the capacitance between the electrodes and the force applied to bring the mobile electrode close to the fixed electrode is measured.

In other words, the bonding force between the electrodes is measured. Said bonding produces a non-linear electromechanical response from the system due to the chemical bonds that are created between the two sensitive layers when they come into contact.

This measuring technique is particularly intended to determine analytes that have two recognition sites for the same specific ligand or for two different ligands or the mobile electrode and the fixed electrode of a combination of two ligands.

In this version, the mobile electrode and the fixed electrode are coated with different ligands or the mobile electrode and the fixed electrode are coated with a combination of two ligands.

Other characteristics and advantages of the invention will become more apparent from the following description that is given as a non-limitative example.

DETAILED DESCRIPTION OF THE PREFERRED EMBODIMENT

Figure 1:
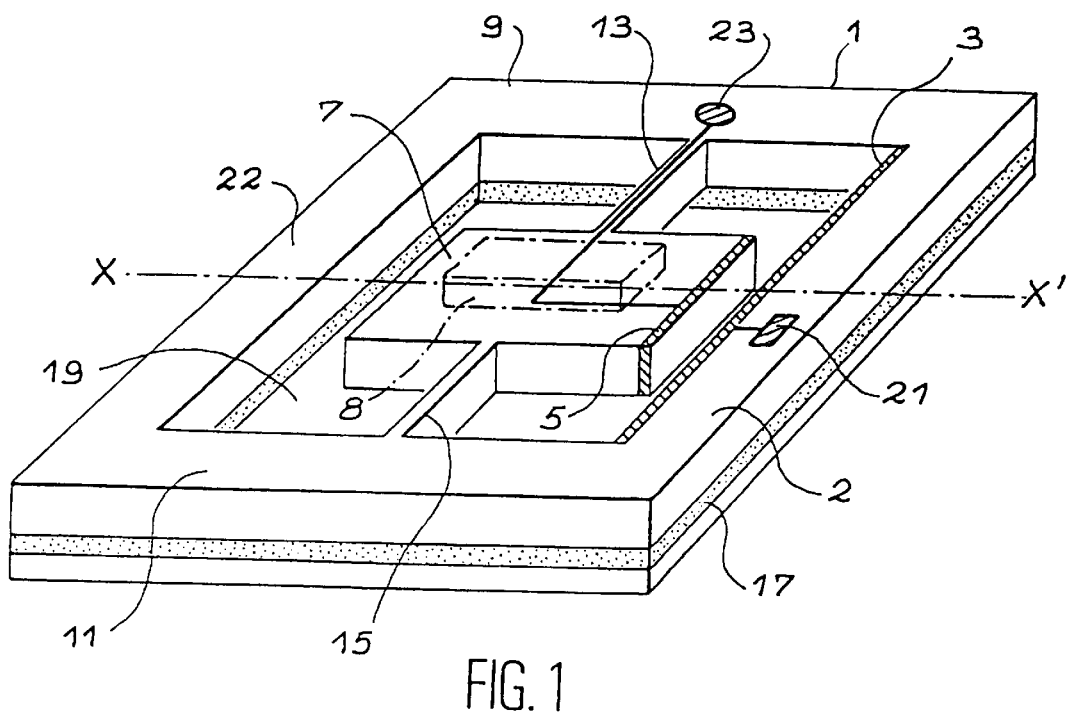
FIG. 1 is a perspective view of a detection apparatus according to the invention.

FIG. 1 shows a perspective view of a microsystem for biological analyses according to the invention.

This microsystem comprises a rectangular box-shaped cell 1 that includes a fixed electrode 3 on one of its lateral surfaces 2. A mobile electrode 5 is located opposite fixed electrode 3 on a mobile part 7 that is mounted on opposite lateral surfaces 9 and 11 of the cell using thin flexible beams 13 and 15 that constitute a flexible mechanical link between mobile part 7 and surfaces 9 and 11.

The fixed electrode 3 and mobile electrode 5 are electrically isolated from each another by an electrical insulating layer 17 positioned on lateral surfaces 2, 9, 11 and 22 of the cell above cell bottom 19.

The inside of the cell constitutes a receiving cavity for the liquid sample to be analysed.

Electrical contacts 21 and 23 connect fixed electrode 3 and mobile electrode 5 respectively to an external circuit.

Said external circuit is used to apply suitable voltages to be applied to the fixed electrode and the mobile electrode, to control the displacement of mobile part 7 and the electrode 5 to which it is fitted, to control the distance between the electrodes, and to take various measurements such as the capacitance measurement between the electrodes, possibly against time and during the displacement of the mobile electrode.

Figure 2:
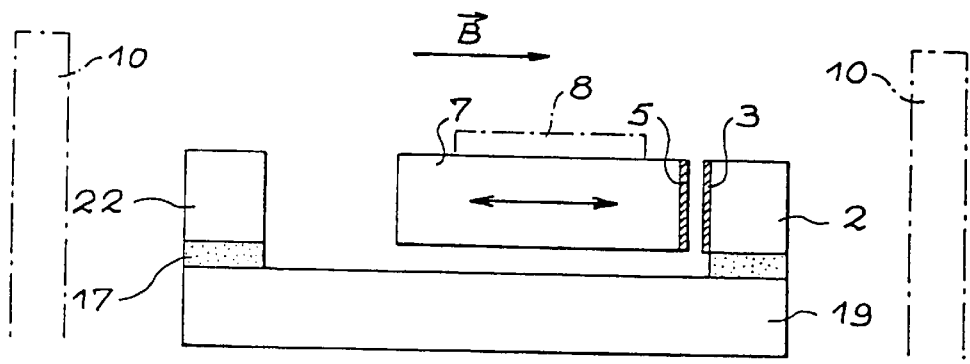
FIG. 2 is a vertical cross-section of the apparatus of the invention along line X–X' in FIG. 1.

FIG. 2 shows a cross-section of the microsystem of the invention at XX' in FIG. 1.

In this figure, where the parts have the same reference numbers, mobile part 7 fitted to mobile electrode 5 is shown in the close position to fixed electrode 3.

In FIGS. 1 and 2 mobile part 7 and electrode 5 to which it is fitted are intended to be displaced when suitable voltages are applied to electrodes 3 and 5. If magnetic means are preferred in order to achieve displacement, the broken lines shown on the apparatus of FIGS. 1 and 2 are modified.

A permanent magnet 8 is positioned on mobile part 7 (shown by a mixed dash/dotted line in FIGS. 1 and 2) and a magnetic field $\vec{B}$ is created around the apparatus, for example using an electromagnet 10 (shown as a dotted line in FIG. 2). In this way magnet 8 and mobile part 7 to which it is fitted are displaced as a result of magnetic field $\vec{B}$.

The microsystem of the invention can be achieved using micromachining procedures such as those used in microelectronics. Extremely small apparatuses can thus be produced, for example 3 mm×3 mm on the sides with a space between the electrodes that can vary between 0.1 $\mu$m in the close position to 10 $\mu$m in the remote position.

Figure 3:
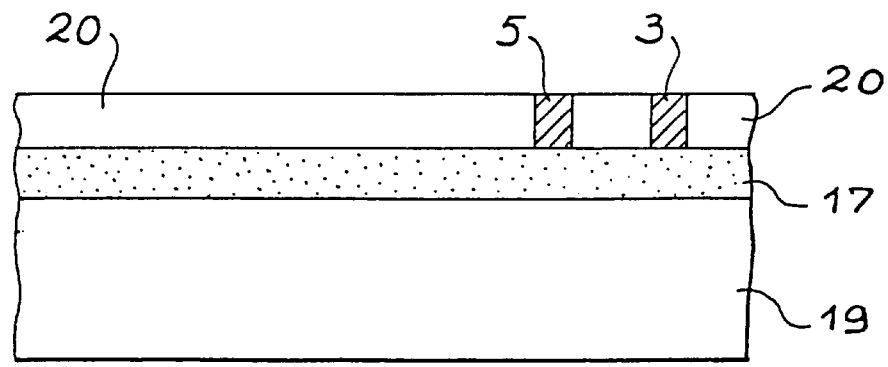
FIGS. 3 to 5 show the main preparation stages of the apparatus of FIG. 1.
Figure 4:
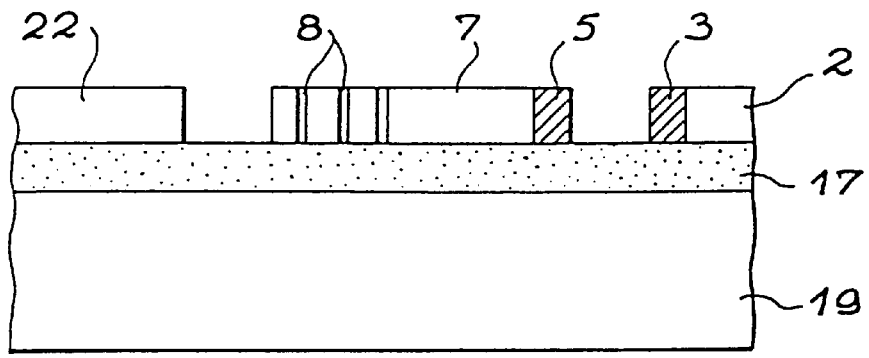
Figure 5:
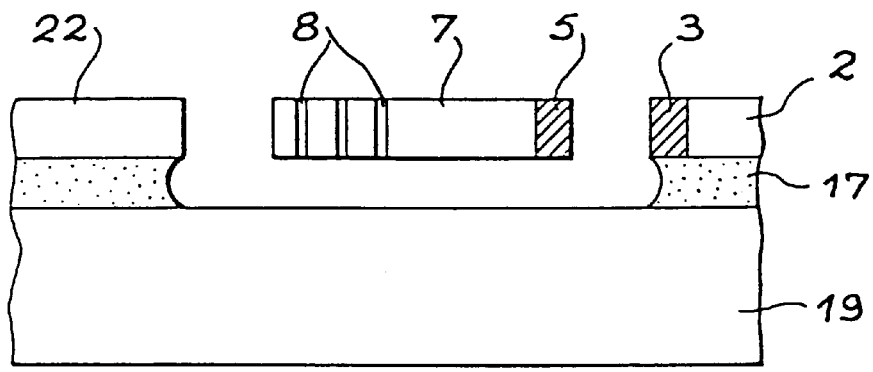

In FIGS. 3 to 5 a microsystem of this kind is schematically shown that is based on SOI (Silicon On Insulator) type substrate.

FIG. 3 shows the first stage of the formation of electrodes 3 and 5 in the SOI substrate that comprises an intermediary layer silica 17 that is approximately 4000 Å thick and that lies between the lower silicon section 19 and the upper section 20, also made of silicon and that is approximately 5 mm thick. To form electrodes 3 and 5, the silicon is modified locally in upper section 20 by implanting ions, for example boron ions, through a mask that constitutes the zones to be implanted and that correspond to the electrodes. In order to achieve the implantation, sufficient power is used to render the silicon a conductor in the zones up to the intermediary silica layer 17.

External electrical contacts 21 and 23 are achieved using standard techniques such as those generally used in microelectronics, for example using metallic gold deposition or continuous etching.

The lateral surfaces 2, 9, 11 and 22, flexible beams 13 and 15 and the mobile part 7 of the apparatus are then achieved using photolithography, as shown in FIG. 4.

This can be achieved using reagent ionic etching (dry etching) of the silicon, for example by means of $SF_6$, down to the layer of silica 17 in the required motif using, for example, a resin mask according to standard techniques. The following components are thus obtained: lateral surface 22, mobile part 7 comprising electrode 5 and lateral surface 2 that is fitted with the fixed electrode 3, lateral surfaces 9 and 11 and thin flexible beams 13 and 15 (not shown in FIG. 4).

Preferably, holes 8 are also made in part 7, using photolithography, that will subsequently be used to free mobile part 7 from bottom 19.

In FIG. 5 the stage of the method is shown in which mobile part 7 is freed. This can be achieved by dissolving the $SiO_2$ layer that coats bottom 19 using hydrofluoric acid that enters via the openings previously provided between the mobile part 7 and the lateral surfaces 2 and 22 and also via holes 8. Layer 17 is thus eliminated except on surfaces 2, 22, 9 and 11 of the apparatus.

The techniques used in the various stages of production of the microsystem are those used in microelectronics. The stage that consists in freeing the mobile part (FIG. 5) can be achieved using the method described in reference 5: 6 EP-A-605 300.

The use of microtechnologies enables the following:
- to heighten the sensitivity of the apparatus (accurate control of the geometry and optical or electrical parameters),
- to improve the detection specificity by using several apparatuses of the same kind on a single silicon plate (redundancy, multiple detection),
- to improve the detection reliability by eliminating problems of localized pollution or non-specific reactions, and
- to obtain reduced production costs by miniaturizing the sensitive parts and using collective hybridization and packaging techniques developed for microsystems.

Therefore, the apparatuses produced using microtechnology techniques provide the final users, particularly decentralized analysis laboratories, the advantage of being extremely practical.

The microsystem shown in FIGS. 1 and 2 can be used for analyses, particularly for biological analyses, once a specific ligand L of the analyte A to be detected has been bonded onto one or both electrodes.

Ligand L can be bonded using standard techniques, for example by adsorption onto the electrode once it has been very lightly oxidized or by creating a covalent connection between the electrode and the ligand using a bifunctional coupling reagent that is capable of reacting with both the electrode and the ligand.

The use of such reagents is well-known. As an example of a reagent suitable for coupling ligands constituted by antibodies, proteins and peptides on the silicon, silane derivatives comprising an alkoxysilane group and an $NH_2$ group may be referred to, the groups being separated by a hydrocarbonated chain. These kinds of techniques are described in references 1, 3 and 4 mentioned above.

Said bonding can also be achieved using the techniques described in WO-A-94/22889 (reference 6).

Said bonding is preferably effected before use and with electrodes 3 and 5 in the remote position.

Figure 6:
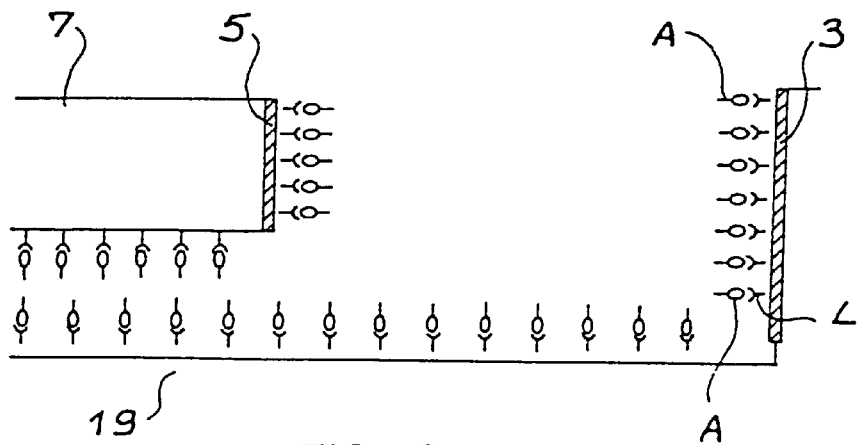
FIG. 6 is a schematic drawing of the apparatus of FIG. 1 during the stage in which the apparatus is coated with electrodes and is brought into contact with the sample, the electrodes being in a remote position.

FIG. 6 is a schematic drawing of electrodes 3 and 5 and a section of bottom 19 and of mobile part 7 of the apparatus of FIG. 1. The electrodes are in the remote position, at a remote distance $d_e$, for example 2 $\mu$m, and they are coated with a specific ligand L.

In order to achieve this bonding the reagents and the ligand are positioned in the container; this results in the ligand also being bonded to bottom 19 and to mobile part 7, as shown in this figure.

Once the ligand has been bonded, the sample to be analysed is positioned in the apparatus, the electrodes remaining in the remote position. If the sample contains the analyte A, said analyte constitutes a complex LA with ligand L or an active layer, the thickness of which is less than 1000 Å on the surfaces of the electrodes and on the apparatus, as shown in FIG. 6.

The presence or otherwise of said complex is then verified, for example by bringing mobile electrode 5 close to fixed electrode 3 in order to obtain a close distance $d_r$ between the electrodes, that is for example 2,000 Å, i.e. 0.2 $\mu$m. A significant parameter is then measured, or is measured when the mobile electrode is brought close to the fixed electrode.

Figure 7:
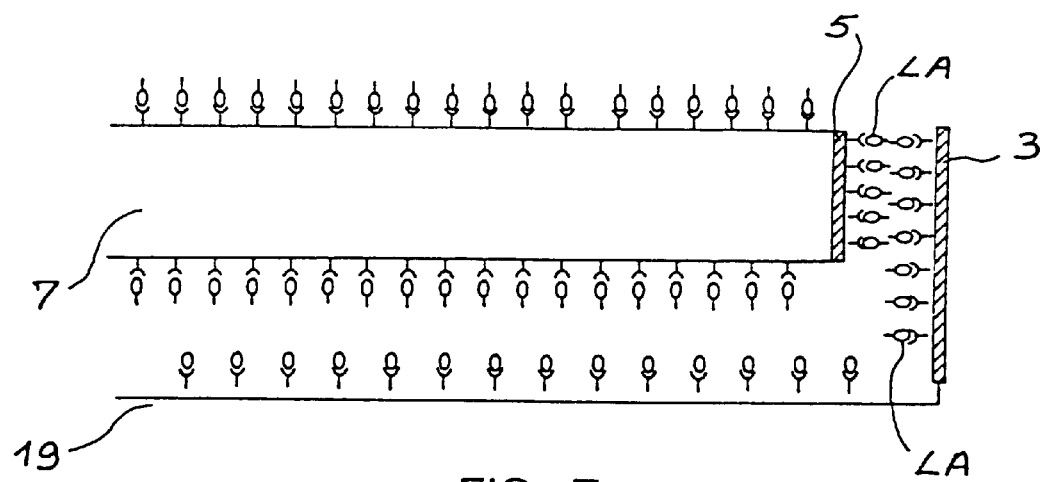
FIG. 7 shows the apparatus of FIG. 1 with the electrodes in a close position.

FIG. 7 shows the apparatus in this position where the distance between the electrodes $d_r$ corresponds to the close position. Thus, the active layer (L-A complex) is seen to occupy most of the space between the electrodes 3 and 5.

In a first embodiment of the invention this layer is detected using an impedance measurement between electrodes 3 and 5 in the close position.

For this measurement suitable voltage is applied to electrodes 3 and 5 and the intensity of the current passing through the cell is measured. By comparing this measurement with a measurement carried out in the same conditions without analyte, it is possible to verify whether the thickness of the sensitive layer has increased and consequently deduct whether or not analyte is present.

In a second embodiment of the invention analyte is detected in the sample by determining the viscosity of the sensitive layer between the electrodes. In order to achieve this, the mobile part is subject to a series of movements towards and away from the fixed electrode by applying suitable voltages to the electrodes. Then this actuating voltage is no longer applied to the mobile part and a voltage measurement is applied to determine the variations in time in the capacitance between the electrodes; said capacitance depends on the distance between the electrodes and the variations in time result from the damping of the oscillating movement produced by the mobile electrode.

The damping depends on the friction and therefore the viscosity of the layer of molecules between the electrodes, and particularly on the thickness.

Figure 8:
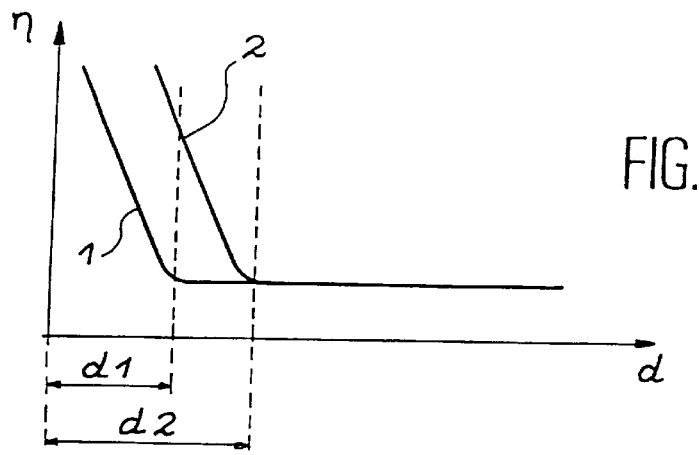
FIG. 8 is a diagram that shows the viscosity of the liquid between the electrodes depending on the distance between the electrodes, with the analyte both absent (curve 1) and present (curve 2).

FIG. 8 shows the development of the viscosity $\eta$ of the liquid relative to the distance d between the electrodes.

Curve 1 of this figure shows the development without an analyte.

Curve 2 shows the development with an analyte.

Both curves show that the viscosity does not vary significantly when the distance between the electrodes remains above the thickness of the layers of ligand alone or the layers of ligand-analyte complex.

On the other hand, when the electrode penetrates the layers the viscosity increases. When no analyte is present and the thickness of the layers is less, said increase is obtained when the distance between the electrodes equals thickness $d_1$.

When analyte is present, this increase in viscosity occurs quicker when the distance between the electrodes has $d_2 > d_1$ thickness because the sensitive layer is thicker than when analyte is absent.

This increase in viscosity can be detected after the mobile electrode has been oscillated between a close position and a remote position by measuring the capacitance variation between the electrodes when the movement of the mobile electrode is dampened. Clearly, the close position must correspond to a distance between electrodes that is less than $d_1$.

In a third embodiment of the invention the analyte is detected by measuring the contact force between the electrodes.

Said third embodiment is particularly used when the analyte comprises two recognition sites for a specific ligand or for two different specific ligands.

Figure 9:
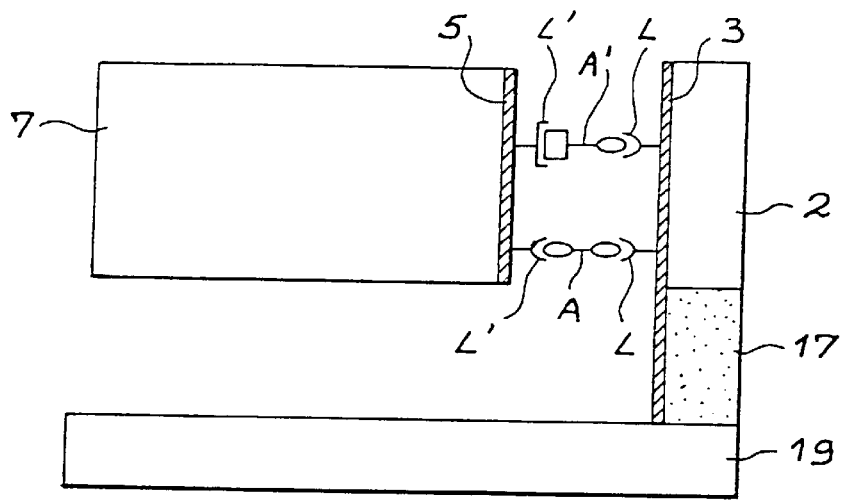
FIG. 9 shows the apparatus of FIG. 1 and the formation of an active layer with an analyte comprising two recognition sites.

This example is illustrated in FIG. 9 where fixed electrode 3 and mobile electrode 5 are shown in close position and are coated respectively with ligands L and L' (L'=L or L'≠L) and analyte A or A' that comprises two identical recognition sites (A) or different recognition sites (A'). Analyte A or A' is connected both to the ligand of electrode 3 and to the ligand of electrode 5. This causes bonding to occur between the electrodes.

Figure 10:
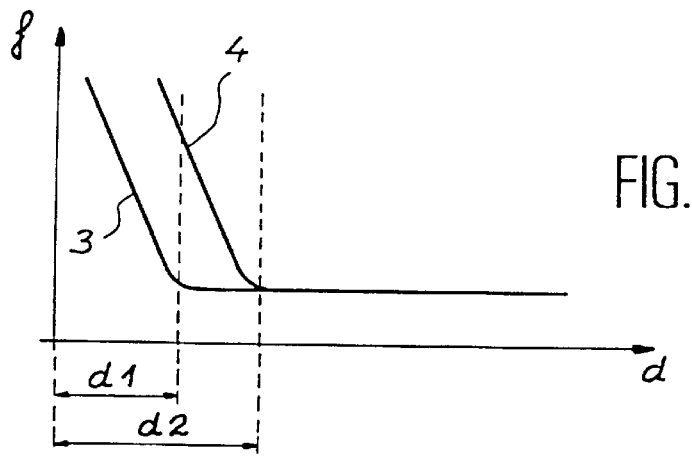
FIG. 10 is a diagram that shows the contact force between the electrodes depending on the distance between the electrodes, with the analyte both absent (curve 3) and present (curve 4).

FIG. 10 shows the contact force f between the electrodes relative to the distance d between the electrodes.

Curve 3 shows this development without an analyte and curve 4 shows the development with an analyte. Therefore, the contact force may be seen to increase quickly when the distance between the electrodes reaches the thickness of the sensitive layer, either $d_1$ without an analyte or $d_2 > d_1$ with an analyte. This also enables the presence of an analyte to be determined.

The contact force can be determined by measuring the capacitance between the electrodes and by measuring the voltage required to bring the mobile electrode to the close position. The value of the capacitance enables the distance between the electrodes to be determined and the force applied is in relation to the thickness of the sensitive layer.

As an example, an apparatus of this kind was used to detect the presence of known DNA sequences in an aqueous solute and using the complimentary DNA sequence as a ligand. The ligand was bonded by being grafted onto a polymer that had, itself, been electrodeposited onto the fixed electrode and the mobile electrode.

References:

(1) Battaillard et al., "Analytical Chemistry", 60, 1988, pages 2,374 to 2,379.
(2) Schyber et al., Sensors and Actuators, B26 and 27, 1995, pages 457 to 460.
(3) FR-A-2 598 227
(4) EP-A-244 326
(5) EP-A-605 300
(6) WO-A-94/22889

What is claimed is:

1. An apparatus for detecting an analyte in a sample, comprising:
   a cell comprising:
      at least one fixed electrode,
      at least one mobile electrode opposite the fixed electrode, the mobile electrode being configured to move with respect to the fixed electrode, and
      a sample receiving cavity defined by a space between said fixed electrode and said mobile electrode,
      wherein a surface of at least one of the fixed electrode and mobile electrode facing the sample receiving cavity is coated with a ligand of the analyte to be detected;
   a displacement mechanism configured to move the mobile electrode; and
   an external circuit connected to said fixed electrode and to said mobile electrode, and configured to measure a parameter having a value depending on the presence between said fixed electrode and said mobile electrode of the analyte to be detected.

2. The apparatus of claim 1, wherein said fixed electrode and said mobile electrode are coated with a ligand of the analyte to be detected.

3. The apparatus of claim 1, wherein the displacement mechanism comprises a polarization mechanism configured to polarize the fixed electrode and the mobile electrode.

4. The apparatus of claim 1, wherein
   the cell comprises a container, said fixed electrode being fastened to one surface of said container,
   the displacement mechanism comprises a mobile part mounted on surfaces of the container by at least one flexible beam, and
   said mobile electrode and said fixed electrode are connected to electrical contacts provided on surfaces of the mobile part and flexible beam.

5. The apparatus of claim 4, wherein the displacement mechanism comprises a polarization mechanism configured to polarize the fixed electrode and the mobile electrode.

6. The apparatus of claim 4, wherein:
   the displacement mechanism comprises a third electrode and a fourth electrode provided on a surface of the container and on the mobile part respectively such that said third and fourth electrodes are positioned opposite each other, and
   said displacement mechanism is configured to polarize said third and fourth electrodes so as to move the mobile electrode.

7. The apparatus of claim 4, wherein the displacement mechanism comprises a magnetic device.

8. The apparatus of claim 7, wherein the magnetic device comprises a permanent magnet positioned on the mobile part and a magnetic field generator configured to apply a magnetic field to said magnet.

9. The apparatus of claim 4, wherein:
   the container has a bottom and lateral surfaces comprising silicon,
   the lateral surfaces are separated from the bottom by a layer of insulating silica,
   the mobile part and the flexible beams comprise silicon, and
   the electrodes comprise silicon with implanted ions.

10. A method for detecting an analyte in a liquid sample, comprising the steps of:
   a) introducing said sample in a cell that comprises at least one fixed electrode and at least one mobile electrode positioned opposite the fixed electrode, said mobile electrode being configured to move with respect to the fixed electrode, at least one of the fixed electrode and the mobile electrode being coated with a ligand of the analyte to be detected, and the liquid sample being positioned between the fixed electrode and the mobile electrode with the mobile electrode being in a remote position from the fixed electrode;
   b) displacing the mobile electrode at least once from the remote position to a close position; and
   c) measuring a parameter having a value depending on the presence of a layer formed from a reaction of the ligand with the analyte to be detected, said layer being between the fixed electrode and the mobile electrode.

11. The method of claim 10, further comprising coating the fixed electrode and the mobile electrode with a ligand.

12. The method of claim 10, wherein measuring said parameter comprises measuring the electrical impedance between the fixed electrode and the mobile electrode after each displacement, and further comprising
   d) comparing the measured electrical impedance to a reference determined in the absence of an analyte.

13. The method of claim 10, wherein:
   displacing the mobile electrode comprises displacing the mobile electrode several times in order for said mobile electrode to oscillate between the close position and the remote position, and
   measuring said parameter comprises measuring the time capacitance between the fixed electrode and the mobile electrode.

14. The method of claim 10, wherein measuring said parameter comprises measuring the capacitance between the fixed electrode and the mobile electrode during displacing the mobile electrode, and further comprises measuring the force applied to bring the mobile electrode closer to the fixed electrode.

15. The method of claim 14, further comprising:
   covering the fixed electrode with a first ligant configured to bind to a first recognition site of the analyte to be detected, and
   covering the mobile electrode with a second ligant configured to bind to a second recognition site of the analvte to be detected.

16. The method of claim 14, further comprising coating the fixed electrode and the mobile electrode with two combined ligands, each configured to bind to a recognition site of the analyte to be detected.

17. The method of claim 10, wherein displacing the mobile electrode is performed so that a maximum distance between the fixed electrode and the mobile electrode is from 1 to 10 $\mu$m and a minimum distance between the fixed electrode and the mobile electrode is from 0.1 to 0.5 $\mu$m.

18. The method of claim 10, further comprising seleting an analyte-ligands pair from a group consisting of antigen-antibody, hapten-antibody, hormone-receptor, $DNA_c$-DNA, $RNA_c$-RNA and enzyme-substrate, said layer between the fixed electrode and the mobile electrode comprising said analyte-ligands pair.

19. A method of manufacturing the apparatus of claim 9, comprising the steps of:
   1) forming electrical conducting zones on a silicon substrate comprising an embedded layer of silica, said electrical conducting corresponding to the fixed and mobile electrodes and being created by the implantation of ions through a mask;
   2) etching the substrate down to the embedded silica layer in order to form, surfaces of the container, the mobile part and the flexible beams;
   3) eliminating the embedded silica layer except for sections that constitute the surfaces of the container;
   4) forming electrical contacts on the surfaces of the container and the flexible beam that connect the fixed and mobile electrodes separately to the external circuit; and
   5) bounding a ligand on a surface of at least one of the fixed electrode and mobile electrode.

* * * * *